United States Patent [19]

Sodickson et al.

[11] Patent Number: 5,724,268

[45] Date of Patent: Mar. 3, 1998

[54] APPARATUS AND METHODS FOR THE ANALYTICAL DETERMINATION OF SAMPLE COMPONENT CONCENTRATIONS THAT ACCOUNT FOR EXPERIMENTAL ERROR

[75] Inventors: Lester Sodickson, Waban; Ronald S. Scharlack, Brookline, both of Mass.

[73] Assignee: Chiron Diagnostics Corporation, E. Walpole, Mass.

[21] Appl. No.: 496,724

[22] Filed: Jun. 29, 1995

[51] Int. Cl.$^6$ ............................. G06F 17/11; G01N 21/84
[52] U.S. Cl. ........................... 364/571.02; 364/498
[58] Field of Search ............ 364/571.01, 571.02–571.06, 364/497, 498

[56] References Cited

U.S. PATENT DOCUMENTS

| | | | |
|---|---|---|---|
| 4,866,644 | 9/1989 | Shenk | 364/571.02 |
| 5,121,337 | 6/1992 | Brown | 364/498 |
| 5,121,338 | 6/1992 | Lodder | 364/498 |
| 5,243,546 | 9/1993 | Maggard | 364/571.02 |
| 5,592,290 | 1/1997 | Arai et al. | 364/571.02 |

OTHER PUBLICATIONS

Kalivas JH and Kowalski BR. Compensation for drift and interferences in multicomponent analysis, Anal Chem 1982, 54, 560–5.

Owen AJ. Quantitative UV–Visible analysis in the presence of scattering, HP publication #12-5963-3937E, 1995.

Blanco M, Coello J, Iturriaga H, Maspoch S, and Rovira E. Wavelength calibration transfer between diode array UV–Visible spectrophotometers, Appl Spectros 1995, 49, 593–7.

Wang Y, Veltkamp DJ, and Kowalski BR. Multivariate instrument standardization. Anal Chem 1991, 63, 2750–6.

Wang Y, and Kowalski BR. Calibration transfer and measurement stability of near–infrared spectrometer, Appl Spectros 1992, 64, 764–71.

Wang Y, and Kowalski BR. Improvement of multivariate calibration through instrument standardization. Anal Chem 1992, 64, 562–4.

Wang Y, and Kowalski BR. Temperature–Compensating calibration transfer for near–infrared filter instruments. Anal Chem 1993, 65, 1301–1303.

Bouveresse E, and Massart DL. Modified algorithm for standardization of near–infrared spectrometric instruments, Anal Chem 1995, 67, 1381–9. Their reference 3 may also be of interest.

Saxberg EH, and Kowalski BR. Generalized Standard Addition Method, Anal Chem 1979, 51, 1031–8.

(List continued on next page.)

*Primary Examiner*—James P. Trammell
*Assistant Examiner*—Kyle J. Choi
*Attorney, Agent, or Firm*—Arthur S. Morgenstern; Gordon Moriarty; Robert P. Blackburn

[57] ABSTRACT

The present invention provides apparatus and methods for determining the concentration of sample components of a sample by an analytical technique that yields a spectrum that can be written as $Y(\omega) = P(\omega) \cdot C$. The apparatus and methods of the invention account for experimental errors that give rise to distortions in the observed spectrum and that consequently result in inaccurate determinations of sample component concentrations. The invention accounts for such errors by modeling the total experimental error as the sum of one or more types of errors that can be written as $\xi \cdot K$. The spectrum is then modeled as $Y = P \cdot C + \xi \cdot K$. Using the observed spectrum, known values for P, and a mathematical model for $\xi$, this equation can be solved for the best fit value of the sample component concentrations, C, and the magnitudes of the errors, K. The method can be used for any error that can be modeled in the foregoing manner, such as a shift in the spectrum. Particular types of shift include constant shift as well as linear shift across the entire spectrum. The apparatus and methods are advantageously used in absorbance spectroscopy and chromatography.

18 Claims, 2 Drawing Sheets

OTHER PUBLICATIONS

Clemen J, Jochum P, and Kowalski BR. Error Propogation and Optimal Performance in Multicomponent Analysis, Anal Chem 1981, 53, 85–92.

Nyden, M.R. et al., "Spectroscopic Quantitative Analysis of Strongly Interacting Systems: Human Plasma Protein Mixtures", *Applied Spectroscopy*, vol. 42, No. 4, pp. 588–594 (1988).

Host, H. "Comparison of Different Calibration Methods Suited for Calibration Problems with Many Variables", *Applied Spectroscopy*, vol. 46, No. 12, pp. 1780–1784 (1992).

de Noord, Onno E., "Multivariate Calibration Standardization", *Chemometrics and Intelligent Laboratory Systems*, vol. 25, No. 2, pp. 85–97 (1994).

APPARATUS AND METHODS FOR THE ANALYTICAL DETERMINATION OF SAMPLE COMPONENT CONCENTRATIONS THAT ACCOUNT FOR EXPERIMENTAL ERROR

BACKGROUND

1. Field of the Invention

The present invention relates to the field of analytical spectrometry and, in particular, to apparatus and methods of correcting for determining analytical sample component concentrations that account for instrumental error.

2. Summary of the Related Art

A wide variety of analytical techniques have been developed over the years to detect and determine the concentrations of components of a sample. Some techniques are entirely spectrophotometric, such as ultraviolet-visible-infrared (UV-VIS-IR) absorbance spectroscopy and NMR spectroscopy. Other techniques, such as column chromatography, are not spectrophotometric per se, but often use spectrophotometric techniques to detect the presence of compounds.

Each of these techniques generally provides a "spectrum" in which a dependent variable, typically the intensity of some quantity (e.g., absorbance), is plotted against a dependent variable (e.g., wavelength). Relative concentrations of sample components are determined by obtaining the best fit to the experimental spectrum by varying the relative spectral contribution of each component. This requires knowledge of the spectral features of the individual components. Owing to instrumental errors and/or deviations in experimental conditions, small shifts of the independent variable often occur that can lead to large changes in the relative concentrations of sample components determined from the measured spectra. To date, the prior art is devoid of suitable methods for determining the shift and correcting for it. Accordingly, new methods of accounting for shifts of the independent variable in analytical spectrophotometric techniques are desirable.

SUMMARY OF THE INVENTION

The present invention provides apparatus and methods for the accurate determination of sample component concentrations. The apparatus and methods of the invention advantageously correct for experimental errors (including instrument induced errors) that would otherwise introduce errors into the measured sample component concentrations. The present invention compensates for a wide variety of phenomena exogenous to the analytical sample that contribute to and are manifested in the observed analytical spectrum, from which sample component concentrations are determined.

The present invention can be employed advantageously in analytical spectrophotometric techniques such as UV-VIS-IR spectroscopy and NMR spectroscopy. The present invention can also be used in analytical techniques that are not spectrophotometric per se, but which incorporate spectrophotometric detection and/or yield a "spectrum-like" graph (i.e., a graph that resembles a spectrum). An example of a technique that yields a "spectrum-like" graph is column chromatography, in which materials are detected by absorbance spectroscopy at one (or more) wavelength, yielding a "spectrum-like" graph that depicts the intensity of the eluate absorbance as a function of time. As used herein, the term "spectrum" encompasses traditional spectrophotometric spectrum wherein a spectral intensity is plotted against radiation frequency, wavelength, or wavenumber (or some equivalent thereof), as well as "spectrum-like" graphs produced in techniques such as column chromatography.

Under ideal conditions, an analytical spectrum can be described by the equation $$Y(\omega)=P(\omega) \cdot C, \quad (i)$$

were $\omega$ is a functional parameter (e.g., frequency, wavelength, wavenumber, or time), Y is a vector whose elements are the spectral intensities, C is a vector whose elements are the concentrations of the sample components, and P is a matrix whose elements are a measure of the magnitude of the contribution of each sample component to the spectral intensity at each value of $\omega$. The elements of P are known quantities and can be, for example, the UV-VIS-IR extinction coefficients of each sample component at each wavelength $\lambda$. In practice, when one desires to use such analytical spectra to determine the concentrations of sample components that give rise to the observed spectrum, $Y_{obs}$, equation (i) can be used to obtain a best fit estimate of C by using $Y_{obs}$ in place of Y.

Owing to instrumental and other experimental errors, however, equation (i) frequently does not describe the observed spectrum well. In that case, equation (i) can be modified to incorporate a term representing the experimental error:

$$Y=P \cdot C+dY, \quad (ii)$$

where dY is the experimental error-induced deviation of the observed spectrum from the ideal. In the present invention, dY is written as:

$$dY=\xi \cdot K, \quad (iii)$$

where K is a scalar representing the magnitude of the error and $\xi$ is a vector whose elements are the relative errors at each value of $\omega$. Equation (ii) is then written as $$Y=P \cdot C+\xi \cdot K. \quad (iv)$$

The apparatus and methods of the present invention can be used to correct for experimental errors whenever the observed spectrum can be written in the form of equation (iv), i.e., whenever the experimental error can be written as in equation (iii). Equation (iv) is readily solved for the best fit sample component concentrations, C, and the magnitude of the error, K, to the observed spectrum, $Y_{obs}$, (using $Y_{obs}$ in place of Y in equation (iv)) as described more fully below.

In one aspect of the invention, the apparatus and methods model the error, dY, as a shift of the entire spectrum by an amount $d\omega$. In this aspect of the invention:

$$dY=\frac{\partial Y}{\partial \omega} d\omega = Y'd\omega. \quad (v)$$

In this aspect of the invention, the observed spectrum is estimated as:

$$Y_{obs}=P \cdot C+Y'd\omega. \quad (vi)$$

Depending on the model chosen for the shift, $d\omega$ can be a scalar (i.e., the same for all $\omega$) or a vector whose elements vary with $\omega$.

In one embodiment of this aspect of the invention, using an appropriate model for $d\omega$, equation (vi) takes the form of equation (iv), which is then solved for the best fit values of C and K.

In another embodiment of this aspect of the invention, the apparatus and methods account for shift due to experimental error by adjusting the entire spectrum (to yield an adjusted spectrum, $Y_{adj}$) using some weighted average $\overline{d\omega}$ of previously determined values of the shift, $d\omega$. The entire spectrum is then adjusted by $\overline{d\omega}$:

$$Y_{adj} = Y_{obs}(\omega + \overline{d\omega}). \qquad \text{(vii)}$$

When $\overline{d\omega}$ is small, $Y' \overline{d\omega}$ is a good estimate of the shift in the spectrum, which is then preferably calculated from:

$$Y_{adj} = Y_{obs} + Y'\overline{d\omega}. \qquad \text{(viii)}$$

On the other hand, when $\overline{d\omega}$ is large, it is preferable to account for the shift by using equation (vii) directly. In either case, in this embodiment of the invention, $Y_{adj}$ is used in either equation (i) or (vi) to obtain the best fit value of C.

In another embodiment of this aspect of the invention, the form of Y in equation (i) is used in equation (v) to obtain an expression for dY in terms of the derivative to P with respect to ω:

$$dY = \frac{\partial Y}{\partial \omega} d\omega = \frac{\partial P \cdot C}{\partial \omega} d\omega = \frac{\partial P}{\partial \omega} \cdot C d\omega, \qquad \text{(ix)}$$

and the estimated spectrum is:

$$Y_{est} = P \cdot C + P' \cdot C \, d\omega \qquad \text{(x)}$$

Equation (x) reduces to the form of equation (iv) when $d\omega$ is modeled appropriately and can then be solved for C.

In another embodiment of this aspect of the invention, the apparatus and methods of the present invention account for shift adjusting P using some weighted average of previously determined values of $d\omega$. An adjusted value of P that accounts for the shift is then given by:

$$P_{adj} = P \, (\omega + \overline{d\omega}). \qquad \text{(xi)}$$

If $\overline{d\omega}$ is large, equation (xi) is preferably used directly. If $\overline{d\omega}$ is small, however, $(\partial P/\partial \omega)d\omega$ is a good estimate of the shift-induced change in P, and $P_{adj}$ is then preferably obtained from:

$$P_{adj} = P + \frac{\partial P}{\partial \omega} d\omega. \qquad \text{(xii)}$$

In either case, $P_{adj}$ is then used in either equation (i) or (x) to obtain the best fit value of C.

In this aspect of the invention, the shift can be modeled in a number of ways. In one embodiment, the shift is modeled as being constant across the entire spectrum. In this model $d\omega = S$, a scalar. In another embodiment, the shift is modeled as varying linearly about a central value of $\omega$, $\omega_c$, and is given by the vector whose elements are $d\omega_i = (\omega_i - \omega_c)M$, where M is the magnitude of the shift. In this embodiment, $d\omega$ is a vector. When M>0 the entire spectrum is magnified about $\omega_c$; when M<0, the entire spectrum is compressed about $\omega_c$. In yet another embodiment, the experimental shift is modeled as a linear combination of the two foregoing models.

As described more fully below, each of these models can account for errors in observed spectrum that are manifested by shifts in ω. The apparatus and methods of the present invention incorporate the foregoing equations to compensate for experimental shift in observed spectra and thereby yield more accurate measurements of the sample component concentrations.

In a particularly preferred embodiment of the present invention, the apparatus and methods of the invention employ UV-VIS-IR absorbance spectroscopy. Co-oximeters, which measure the relative concentrations of blood components, are an example of one embodiment. In this embodiment, Y is the absorbance spectrum A, P is the matrix of extinction coefficients, E, and the independent variable, ω, is the wavelength, λ.

In another preferred embodiment, the apparatus and methods of the invention employ chromatographic means. In this embodiment, ω is the time at which the sample components elute, Y is the absorbance at the wavelength at which the components are detected, and P is a matrix of the relative absorbances of each sample component as a function of elution time.

DESCRIPTION OF THE DRAWINGS

The invention will be more fully understood from the following detailed description taken in conjunction with the accompanying drawings in which.

DETAILED DESCRIPTION OF THE PREFERRED EMBODIMENTS

Figure 1:
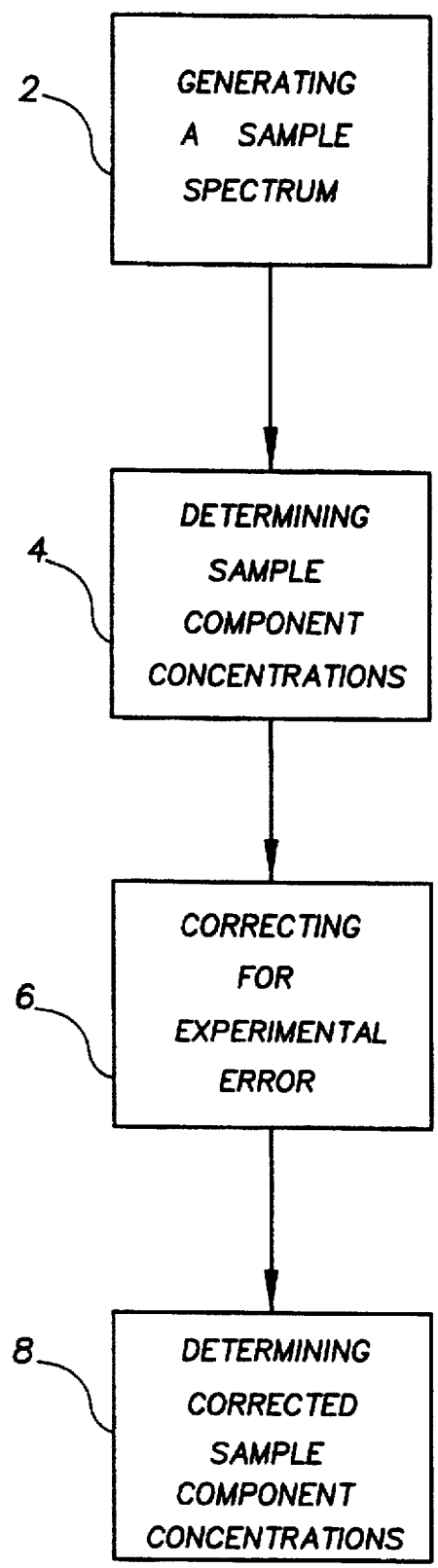
FIG. 1 is a flow chart of the presently disclosed method.
Figure 2:
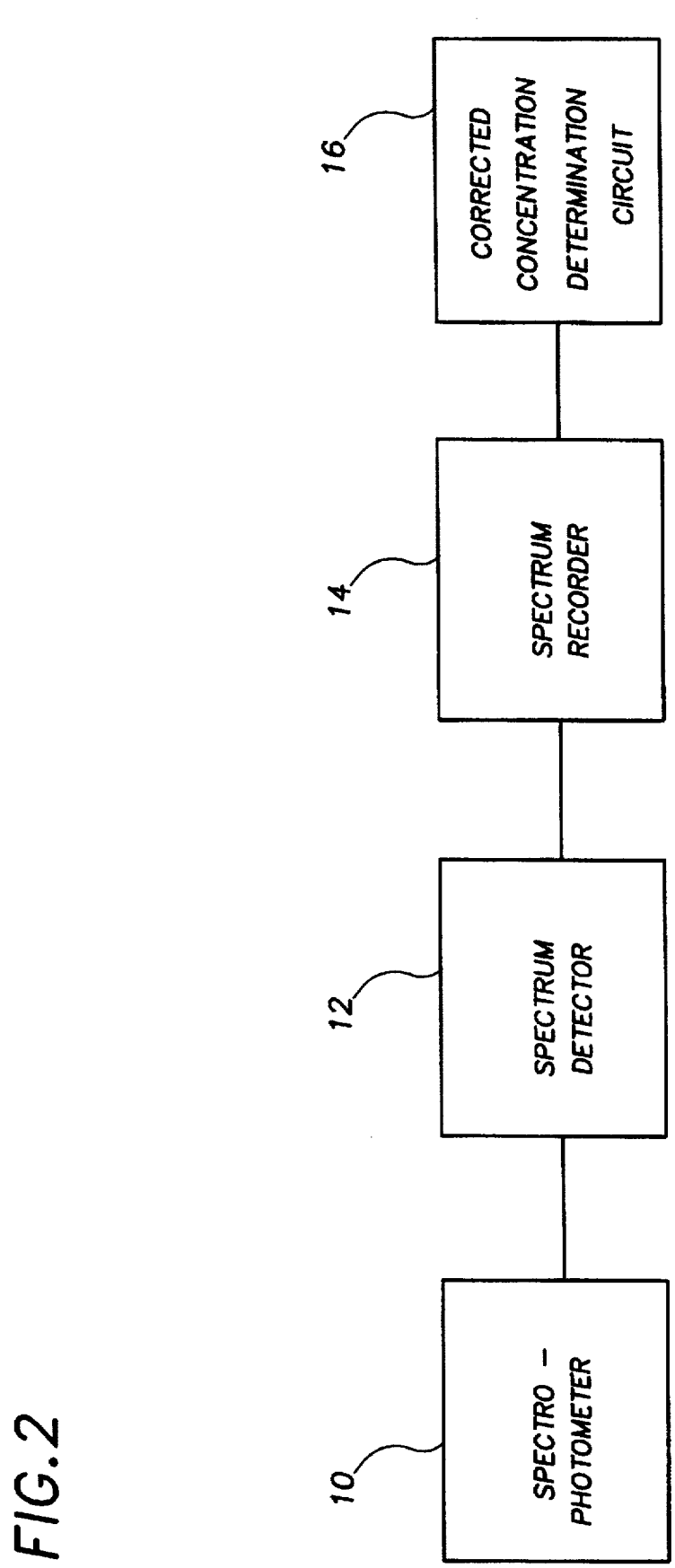
FIG. 2 is a block diagram of the apparatus of the present invention.

The apparatus and methods of the present invention, as shown in FIGS. 1 and 2, are useful for correcting for a wide variety of instrumental and other experimental errors in a wide variety of spectrophotometric and analytical techniques. FIG. 1. shows flow chart including a first step 2 for generating a sample spectrum, a second step 4 for determining sample component concentrations, a third step 6 of correcting for experimental error and a fourth step 8 for determining corrected sample component concentrations. FIG. 2 shows the apparatus of the present invention which includes a spectrophotometer 10, along with a spectrum detector 12, a spectrum recorder 14 and a corrected concentration determination circuit 16. In general, the apparatus and methods of the present invention can be used in conjunction with any spectrophotometric and/or analytical technique yielding a spectrum that can be described by the equation:

$$Y(\omega) = P(\omega) \cdot C, \qquad (1)$$

where Y is a vector whose "m" components $Y_i$ are the intensities of the spectrum at each of the "m" values of the independent variable $\omega(\omega_i)$, C is a vector whose "n" elements are the concentrations of the sample components that contribute to the measured response Y, and P is an "m×n" matrix whose elements $P_{ij}$ relate the contribution of component $C_j$ to the intensity $Y_i$. "m" is an integer and equal to the number of values at which Y is measured. "n" is also an integer and equal to the number of sample components contributing to Y. In UV-VIS-IR spectroscopy, for example, $Y_i$ is the sample absorbance at wavelength $\omega_i$, and the $P_{ij}$ are the extinction coefficients of absorbant "j" at wavelength $\omega_i$. In column chromatography, as another example, $Y_i$ is the intensity of the absorbance at time $\omega_i$, and the $P_{ij}$ are the extinction coefficients of the absorbant "j" at the monitoring wavelength at elution time to $\omega_i$ under the particular elution conditions (e.g., buffer identity and strength, pH, temperature, etc.). In practice, when one desires to use such an analytical spectrum to determine the best estimate of sample components concentrations, equation (1) can be used by inserting $Y_{obs}$ for Y and solving for the best fit value of C.

As will become clearer below, it will be appreciated by those skilled in the art that the present apparatus and methods are ideally suited to analytical techniques in which the identity of the "n" sample components and the matrix elements of P are known and it is desired to determine the best estimate concentrations of the sample components from the observed (measured) spectrum $Y_{obs}$.

The present apparatus and methods can be employed advantageously in analytical spectrophotometric techniques such as UV-VIS-IR spectroscopy and NMR spectroscopy. The present methods can also be used in analytical techniques that are not spectrophotometric per se, but which incorporate spectrophotometric detection and/or yield a "spectrum-like" graph (i.e., a graph that resembles a spectrum). An example of a technique that yields a "spectrum-like" graph is column chromatography, in which materials are detected by absorbance spectroscopy at one (or more) wavelength, yielding a "spectrum-like" graph that depicts the intensity of the eluate absorbance as a function of time. As used herein, the term "spectrum" encompasses traditional spectrophotometric spectrum wherein a spectral intensity is plotted against radiation frequency, wavelength, or wavenumber (or some equivalent thereof), as well as "spectrum-like" graphs produced in techniques such as column chromatography.

It is frequently the case that errors in the observed spectrum are introduced due to less than ideal instrument performance and/or experimental technique. As used herein, the term "experimental error" means any error (e.g., arising from less than ideal instrument performance or suboptimal experimental technique) resulting in a deviation of the measured spectrum from the theoretical ideal. These errors translate into errors in the measured sample component concentrations. These errors in the observed spectrum can be accounted for by rewriting equation (1) as $$Y_{obs} = P \cdot C + dY, \qquad (2)$$

where dY is the experimental error-induced deviation in $Y_{obs}$ from the ideal. The present apparatus and methods corrects for such errors by incorporating a mathematical model for dY:

$$dY = \xi \cdot K \qquad (3)$$

where K is a vector of dimension "r" whose elements are the magnitudes of the errors for each of the "r" types of error modeled as contributing to the spectrum, and $\xi$ is an "m×r" matrix comprised of "r" vectors each of whose "m" elements are the relative errors at each value of ω for each type of error modeled as contributing to the spectrum. "r" is an integer and equal to the number of types of errors modeled as contributing to the spectrum. Where only one type of error is modeled r=1, and K is a scalar and $\xi$ is a vector.

Equation (3) is then written as:

$$Y_{obs} = P \cdot C + \xi \cdot K \qquad (4)$$

In its broadest aspect, the apparatus and methods of the present invention incorporate corrections for instrumental and/or other experimental induced errors in measured spectra whenever the spectra can be written in the form of equation (4).

In this aspect, therefore, the invention comprises an improved apparatus and methods of determining the concentrations of sample components using an analytical technique that yields a spectrum that can be estimated as equation (1), the improvement comprising correcting for experimental error by modeling the experimental error as "r" types of errors given by the product $\xi \cdot K$, where K is a vector whose "r" elements are the magnitudes of each of the "r" types of experimental errors and $\xi$ is an "m×r" matrix whose elements are the relative errors at each value of ω for each type of experimental error, adding the product $\xi \cdot K$ to the estimated spectrum as in equation (4), and solving for the best fit values of C and K.

As used in the present invention $r \geq 1$; preferably $r \leq 10$; and most preferably $1 \leq r \leq 3$. $n \geq 1$ and preferably $1 \leq n \leq 20$. $m \geq n+r$ and preferably m is about twice n+r.

Equation (4) is readily solved for the best fit values of C and K by least squares analysis. To do so, equation (4) is "collapsed" by defining an "m×(n+r)" augmented matrix, $P_\xi$, which has the form:

$$P_\xi = \begin{bmatrix} P_{1,1} & \cdots & P_{1,n} & \xi_{1,1} & \cdots & \xi_{1,r} \\ \cdot & & \cdot & \cdot & & \cdot \\ \cdot & & \cdot & \cdot & & \cdot \\ \cdot & & \cdot & \cdot & & \cdot \\ P_{m,1} & \cdots & P_{m,n} & \xi_{m,1} & \cdots & \xi_{m,r} \end{bmatrix} \qquad (5)$$

and an augmented vector, $C_K$, of dimension "n+r," which has the form:

$$C_K = \begin{bmatrix} C_1 \\ \cdot \\ \cdot \\ \cdot \\ C_n \\ K_1 \\ \cdot \\ \cdot \\ \cdot \\ K_r \end{bmatrix} \qquad (6)$$

Equation (4) then becomes:

$$Y_{obs} = P_\xi \cdot C_K. \qquad (7)$$

The least squares solution to equation (7) is given by:

$$C_K = P_\xi^\dagger \cdot Y_{obs}, \qquad (8)$$

where $$P_\xi^\dagger = (P_\xi^T \cdot P_\xi)^{-1} \cdot P_\xi^T \qquad (9)$$

is the least squares transformation matrix. E.g., Noble and Daniel, *Applied Linear Algebra*, pp. 57–65 (Prentice-Hall, Inc., N.J., 1977). $C_K$ is readily determined from equation (8) using standard algorithms. See, e.g., Press et al., *Numerical Recipes: The Art of Scientific Computing* (Cambridge University Press, Cambridge 1986). The first "n" elements of $C_K$ are the best fit values of the "n" sample component concentrations and the remaining "r" elements are the best fit magnitudes of the errors.

In another aspect of the invention, the apparatus and methods model the error, dY, as a shift of the entire spectrum by an amount dω. In this aspect of the invention:

$$dY = \frac{\partial Y}{\partial \omega} d\omega = Y' d\omega. \qquad (10)$$

In one embodiment of this aspect of the invention, the spectrum is estimated by substituting equation (10) into equation (2) to obtain $$Y_{obs} = P \cdot C + Y' d\omega. \qquad (11)$$

The term $Y'd\omega$ must be capable of being written in the form of equation (3) and, therefore, equation (11) in the form of equation (4). As will be demonstrated below, this can be so even when $d\omega$ itself is other than a scalar. In that instance, $d\omega$ is decomposed into a scalar K and a vector or matrix and the vector or matrix combined with $Y'$ to form a product matrix $\xi$. Equation (11) is then solved in the same manner described above for equation (4). Specific examples of this method are presented in greater detail below.

In another embodiment of this aspect of the invention, the shift due to experimental error is accounted for by adjusting the entire spectrum using some weighted average of the magnitude of the shift, $\overline{d\omega}$, obtained, for example, from previously determined values of the shift, $d\omega$. The entire spectrum is corrected for experimental error by shifting it by an amount $\overline{d\omega}$:

$$Y_{adj}=Y_{obs}(\omega+\overline{d\omega}). \tag{12}$$

When $\overline{d\omega}$ is large relative to the resolution of the measured spectrum, equation (12) is preferably used directly to obtain the adjusted, corrected spectrum, $Y_{adj}$. When $\overline{d\omega}$ is small relative to the measured spectrum, $Y'\overline{d\omega}$ is a good estimate of the shift in the spectrum, which is then preferably calculated from:

$$Y_{adj}=Y_{obs}+Y'\overline{d\omega}. \tag{13}$$

In either case, however, $Y_{adj}$ is then used in either equation (1), (11), or (19) (see infra) in place of $Y_{obs}$ and the equations solved to obtain the best fit value for C that is corrected for shift.

$\overline{d\omega}$ is any suitable scalar representing the shift in $\omega$. In a preferred embodiment, $\overline{d\omega}$ is the previously calculated value of $d\omega$, or an average over the last "k" measurements, where "k" is 2 or more. In a preferred embodiment, K is 5 or more. In another preferred embodiment, k=8. This method weights each of the last "k" measurements equally. Alternatively, a filter can be used to give greater weight to the most recent values of $d\omega$. In this embodiment, each of the last "k" values of $d\omega$ are weighted by a factor "$w_i$." $d\omega$ is then represented by a vector, $d\omega^*$, where each of the "k" elements $d\omega_i^*$ is a previously determined value of $d\omega$, such that $d\omega_1^*$ is the most recently determined value of $d\omega$ and $d\omega_k^*$ is the oldest value. $\overline{d\omega}$ is then obtained from the equation:

$$\overline{d\omega}=w^T \cdot d\omega^*, \tag{14}$$

wherein $w^T$ is the transpose of the vector $w$ whose "k" values "$w_i$" are chosen such that $w_1 \geq w_2 \geq \ldots \geq w_k$ and;

$$\sum_{i=1}^{k} w_i = 1. \tag{15}$$

w can be determined in any suitable manner. For equal weighting of the last "k" values of $d\omega$, each $w_i$ is 1/k. Alternatively, where it is desired to give greater weight to the most recently determined values of $d\omega$, a function such as:

$$w_i = \frac{1}{a \cdot i} / \sum_{i=1}^{k} \frac{1}{a \cdot i} \tag{16}$$

or $$w_i = \frac{1}{a^i} / \sum_{i=1}^{k} \frac{1}{a^i} \tag{17}$$

can be used, wherein "a" is a real number greater than 0. Preferably "a" is greater than 1. Other suitable weighting functions are well known to those skilled in the art.

In another embodiment of this aspect of the invention, the form of Y in equation (1) is used in equation (10) to obtain an expression for dY in terms of the derivative to P with respect to $\omega$:

$$dY = \frac{\partial Y}{\partial \omega} d\omega = \frac{\partial P \cdot C}{\partial \omega} d\omega = \frac{\partial P}{\partial \omega} \cdot Cd\omega = P' \cdot Cd\omega, \tag{18}$$

and the best fit value of C corrected for shift is obtained from:

$$Y_{obs}=P \cdot C+P' \cdot C \, d\omega. \tag{19}$$

Equation (19) reduces to the form of equation (4) when $d\omega$ is modeled appropriately and an estimated value for C, $C_{est}$, is used in the expression $P' \cdot C$. $C_{est}$ can be obtained, for example, from the solution to equation (1):

$$C_{est}=P^\dagger \cdot Y_{obs} \tag{20}$$

where $$P^\dagger=(P^T \cdot P)^{-1} \cdot P^T \tag{21}$$

is the least squares transformation matrix and $Y_{obs}$ is the observed (or measured) spectrum. With this estimate equation (19) is then solved for the best fit value of C and the magnitude of the shift in the same way equation (4) is solved, as described above.

In another embodiment of this aspect of the invention, the shift is accounted for by adjusting P using some weighted average of previously determined values of $d\omega$. An adjusted value of P that accounts for the shift is then given by:

$$P_{adj}=P(\omega+\overline{d\omega}). \tag{22}$$

If $\overline{d\omega}$ is large, equation (21) is preferably used directly. If $\overline{d\omega}$ is small, however, $P' \, \overline{d\omega}$ is a good estimate of the shift-induced change in P, and $P_{adj}$ is then preferably obtained from:

$$P_{adj}=P+P'\overline{d\omega} \tag{23}$$

In either case, $P_{adj}$ is then used in either equation (1) or (19) in place of P to obtain a value for C that is corrected for shift. In either case, $P_{adj}$ is used in any of equations (1), (11), and (19) to determine the magnitude of the shift, $d\omega$, and a corrected value of C.

The shift can be modeled in a variety of ways. For example, in one embodiment, the shift in $\omega$ is modeled as being constant across the entire spectrum. In this embodiment $d\omega$ is defined as a scalar S, which can be positive or negative. $\overline{d\omega}$ is given by some weighted average, $\overline{S}$, of S. In this embodiment equation (11) takes the form:

$$Y_{obs}=P \cdot C+Y' \cdot S. \tag{24}$$

In this embodiment, the shift can be accounted for to obtain more accurate values of C by solving equation (24) in the manner described for solving equation (4), supra, where $\xi=Y'$ and K=S. Alternatively, the entire spectrum may be shifted by amount S, preferably as in equation (12) when S is large:

$$Y_{adj}=Y_{obs}(\omega+S). \tag{25}$$

or as in equation (13) when S is small:

$$Y_{adj}=Y_{obs}+Y'S. \tag{26}$$

In either case, however, $Y_{adj}$ is then used in either equation (1), (24), or (27) (see infra) in place of $Y_{obs}$ to obtain S and a best fit value of C that is corrected for the shift, Alternatively, the shift is accounted for using the derivative of the matrix P, as in equation (19):

$$Y_{obs} = P \cdot C + P' \cdot CS. \qquad (27)$$

Equation (27) is solved in the same manner as equation (19) to obtain the magnitude of the shift S and a value of C that is corrected for the shift. Or, if a reasonable estimate of $\overline{S}$ is available, equation (22) can be used to correct for the shift by adjusting the matrix P, using:

$$P_{adj} = P(\omega + \overline{S}). \qquad (28)$$

if $\overline{S}$ is large, or:

$$P_{adj} = P + P' \overline{S}. \qquad (29)$$

if $\overline{S}$ is small. In either case, $P_{adj}$ is then used in any of equations (1), (24), and (27) in place of P to obtain a value for C that is corrected for shift. If either equation (24) or (27) is used, a new value for the magnitude of the shift, S, is also obtained.

In another embodiment for modeling experimental error arising from a shift in the spectrum, the shift is modeled as a compression/magnification of the spectrum about a central value of $\omega$, $\omega_c$. The change in $\omega$ due to magnification or compression in this model is given by $$d\omega_i = (\omega_i - \omega_c)M, \qquad (30)$$

where $\omega_i$ is the "$i^{th}$" component of the vector $\omega$, whose elements are the values of $\omega$ at which measurements are taken, and M is the magnification/compression factor. It is seen that in this model d$\omega$ is a vector. If M>0, then the scale of the independent variable $\omega$ is magnified. If M<0, then the scale is compressed. It is seen from equation (30) that the change in $\omega$ for which this method compensates is directly proportional not only to the magnification/compression factor M, but also to the distance from the central value of $\omega$, $\omega_c$. Thus, the greater the distance from the central value, $\omega_c$, the greater the change.

In this embodiment equation (11) takes the form:

$$Y_{obs} = P \cdot C + Y' \cdot \Delta M. \qquad (31)$$

where $\Delta$ is a diagonal matrix whose diagonal elements $\Delta_{ii}$ are $(\omega_i - \omega_c)$. Equation (31) is the same as equation (4), with $\xi = Y' \cdot \Delta$ and K=M, and can be solved in the same manner.

Alternatively, if a reasonable value $\overline{M}$ is available (as described in equations (14)–(17) and associated text), the spectrum may be shifted by amount $\Delta \overline{M}$, preferably as in equation (12) when $\overline{M}$ is large:

$$Y_{adj} = Y_{obs}(\omega_i + (\omega_i - \omega_c)\overline{M}), \qquad (32)$$

or as in equation (13) when $\overline{M}$ is small:

$$Y_{adj} = Y_{obs} + Y' \cdot \Delta \overline{M}. \qquad (33)$$

In either case, however, $Y_{adj}$ is then used in either equation (1), (31), or (34) (see infra) in place of $Y_{adj}$ to obtain M and a best fit value of C that is corrected for the magnification/compression type shift.

Alternatively, the magnification/compression type shift is accounted for using the derivative of the matrix P, as in equation (19):

$$Y_{obs} = P \cdot C + \Delta \cdot P' \cdot CM. \qquad (34)$$

Equation (34) is solved in the same manner as equation (19) (by estimating C in the expression $\Delta \cdot P' \cdot C$, which is equivalent to $\xi$ in equation (4)) to obtain M and a value of C that is corrected for the magnification/compression type shift. Or, if a reasonable estimate of $\overline{M}$ is available (as described in equations (14)–(17) and associated text), equation (34) can be used to correct for the magnification/compression type shift by adjusting the matrix P, using:

$$P_{adj} = P(\omega_i + (\omega_i - \omega_c)\overline{M}). \qquad (35)$$

if $\overline{M}$ is large, or:

$$P_{adj} = P + \Delta \cdot P' \cdot C. \qquad (36)$$

if $\overline{M}$ is small. In either case, $P_{adj}$ is then used in any of equations (1), (31), or (34) in place of P to obtain a best fit value for C that is corrected for the magnification/compression type shift. If either equation (31) or (34) is used, a new value of M is also obtained In yet another aspect of the invention, the apparatus and methods incorporate the foregoing techniques to compensate both for shift and magnification/compression. In this aspect of the invention, the shift, d$\omega$, is given by $$d\omega_i = S + (\omega_i - \omega_c)M. \qquad (37)$$

Using this expression for d$\omega$ in equation (11) yields:

$$Y_{obs} = P \cdot C + Y'S + \Delta \cdot Y'M. \qquad (38)$$

Equation (36) can be solved in the very same manner as equation (4) by defining $\xi$ as the matrix $[Y', \Delta \cdot Y']$ and K as a vector [S,M]. Whereas the previous two embodiments illustrated models to equation (4) in which $\xi$ and K were a vector and a scalar, respectively, this embodiment illustrates a situation in which $\xi$ and K are a matrix and a vector, respectively.

In an alternative embodiment of this aspect of the invention, a weighted average of the scalars S and M are used to precalculate an adjusted spectrum, $Y_{adj}$, using equation (12) wherein $\overline{d\omega}$ is $\overline{S} + (\omega_i - \omega_c)\overline{M}$:

$$Y_{adj} = Y_{obs}(\omega_i + \overline{S} + (\omega_i - \omega_c)\overline{M}) \qquad (39)$$

which is used if the sum $\overline{S} + (\omega_i - \omega_c)\overline{M}$ is large, or:

$$Y_{adj} = Y + Y'\overline{S} + \Delta \cdot Y'\overline{M} \qquad (40)$$

when the sum $\overline{S} + (\omega_i - \omega_c)\overline{M}$ is small. In either case, $Y_{adj}$ is used in any of equations (1), (38) or (41) in place of $Y_{obs}$ to obtain new values for S and M and a best fit value for C that is corrected for both types of shift error.

In another embodiment of this aspect of the invention, the change in $\omega$ due to the combined effects of shift and magnification/compression can be accounted for by calculating the derivative of the matrix P. Using the results previously reported, equations (27) and (34), the estimated spectrum is:

$$Y_{obs} = P \cdot C + P' \cdot CS + \Delta \cdot P' \cdot CM. \qquad (41)$$

Equation (41) is analogous to equation (38) and can be solved in the same manner as equation (4) by defining the matrix $\xi$ as $[P' \cdot C, \Delta \cdot P' \cdot C]$ and the vector K as [S,M].

Alternatively and/or in addition, an adjusted matrix P, $P_{adj}$, can be calculated using previously determined values of $\overline{S}$ and $\overline{M}$. Using equation (22), the adjusted matrix P is given by:

$$P_{adj} = P(\omega_i + \overline{S} + (\omega_i - \omega_c)\overline{M}). \qquad (42)$$

when the sum $\overline{S} + (\omega - \omega_c)\overline{M}$ is large and by equation (23):

$$P_{adj} = P + P' \cdot C + \Delta \cdot P' \cdot C. \tag{43}$$

when $\overline{S} + (\omega - \omega_c)\overline{M}$ is small. In either case, $P_{adj}$ can be used in place of P in any of equations (1), (38), or (41) to obtain a best fit value of C that is corrected for both types of shift. If either equation (38) or (41) are used, new values for S and M are also obtained.

In a particularly preferred embodiment of the present invention, the foregoing methods are applied to analytical absorbance spectroscopy. In this embodiment of the invention, equation (1) is the well known Beer-Lambert law:

$$A_{obs}(\lambda) = E(\lambda) \cdot C, \tag{44}$$

where $A_{obs}(\lambda)$ is the absorbance spectrum measured as a function of the wavelength $\lambda$, $E(\lambda)$ is the matrix of wavelength-dependent extinction coefficients for the absorbents, and C is the concentration of the absorbents. A is a vector whose "m" elements $A_i$ are the absorbencies at "m" discrete wavelengths $\lambda_i$, E is an "m×n" matrix whose elements $E_{ij}$ are the extinction coefficients of component "j" at wavelength $\lambda_i$, and C is a vector, each of whose "n" elements $C_j$ is the concentration of absorbant "j".

Hence, it is seen that in this particularly preferred embodiment, the following correspondences exist:

$$\omega = \lambda \tag{45a}$$
$$Y_{obs} = A_{obs} \tag{45b}$$
$$Y = \frac{\partial A}{\partial \lambda} \tag{45c}$$
$$P = E \tag{45d}$$
$$P' = \frac{\partial P}{\partial \lambda} \tag{45e}$$
$$\Delta_i = (\lambda_i - \lambda_c) \tag{45f}$$

These definitions are then used in equations (1) through (43) to measure the magnitude of the experimental error and calculate a value of C that is corrected for error, as described above.

This embodiment is particularly useful, for example, in analytical UV-VIS-IR absorbance spectrophotometry (e.g., as conducted with the Ciba-Corning Diagnostics 800 Series Co-oximeters) used to determine the concentrations of blood components in blood samples. The major components of blood that will ordinarily be used in the present methods are reduced hemoglobin (HHb), oxyhemoglobin ($O_2$Hb), carboxy hemoglobin (COHb), methemoglobin (MetHb), sulf-hemoglobin (SHb), and lipid. The wavelength-dependent extinction coefficients for hemoglobin-based blood components for use in E can be measured directly (preferably on a highly calibrated spectrophotometer) or obtained from the literature. E.g., Zijlstra et al., *Clin. Chem.* 37(9), 1633–1638 (1991). The lipid spectrum can be measured from intravenous fat emulsion (e.g., the commercially available lipid product intralipid) in an aqueous dispersion of about 10% by weight. In a particularly preferred aspect of the invention, the inventive method is used to correct for instrumental wavelength drift observed in UV-VIS-IR absorbance spectroscopy.

In another embodiment, the foregoing methods are employed to correct for experimental error in column chromatography. In this embodiment, the independent variable $\omega$ is equal to the elution time, t. The spectrum $Y_{obs}$ is the magnitude of the signal for detecting the presence of sample components in the eluate (e.g., absorbance, refractive index). The shape of the elution profile measured under standard and controlled conditions provides the elements of P. In this embodiment, a shift in elution time, dr, is equivalent to the shift in the independent variable, $d\omega$. Such a shift may arise due to deviations from the standard conditions of such parameters as the flow rate, solvent strength, and column temperature. The change in elution time can be modeled as a combination of scalar shift and linear shift, as described in equations (37)–(43) and associated text. For example, a change in column flow rate affects the elution time for unretained components and will change the elution time for retained components in approximate proportion to their initial elution times less the elution time for the unretained components. Therefore, all peaks will be shifted by a fixed delay plus one proportional to the elution time difference.

All of the foregoing mathematical manipulations can be conducted using standard software packages, such as MATHCAD (MathSoft, Cambridge, Mass.).

In all of the methods of the present invention, a sample spectrum is generated from which the sample component concentrations can be determined. The sample component concentrations are then determined by employing one or more of the methods described previously.

The apparatus according to the invention incorporate the methods according to the invention to more accurately determine the concentrations of sample components. Accordingly, the apparatus according to the invention comprises a means for generating a spectrum (as defined hereinabove) of an analytical sample, a means for detecting the spectrum, a means for recording the spectrum, and a means for manipulating the spectrum according to any of the methods described herein. Myriad means for generating, detecting, and recording a spectrum exist and are well known to those skilled in the art. E.g., Hobart H. Willard et at., *Instrumental Methods of Analysis* (7th Ed., Wadsworth Pub. Co., Belmont, Calif., 1988). The means for manipulating the spectrum comprises any computer means that can run software embodying one or more of the foregoing methods for determining sample component concentrations corrected for experimental error from the measured spectrum. Of course, the practitioner will appreciate that the apparatus need not be an integrated unit. In a preferred embodiment, the apparatus is a spectrophotometer capable of generating a sample spectrum in the UV, VIS, or IR regions of the electromagnetic spectrum. In another preferred embodiment, the apparatus comprises column chromatography equipment.

The following examples are provided to illustrate certain embodiments of the invention and are not intended, nor should they be construed, to limit the invention in any manner.

EXAMPLES

All mathematical manipulations described herein were performed using the MATHCAD software by MathSoft (Cambridge, Mass.). Ciba-Corning Diagnostic proprietary extinction coefficient matrices were used.

Example 1

Estimating Wavelength Shift Using the Derivative of the Absorbance Spectrum

The absorbance spectrum of eleven blood samples was measured at a resolution of 1 nm and the fractions of HHb, $O_2$Hb, COHb and MetHb calculated using a least squares solution of equation (1). The results are as follows:

$$\begin{pmatrix} 0.5 & -0.5 & 0.2 & 1.2 & 0.4 & 0 & 0.8 & 0.4 & 2.2 & 0.2 & -0.4 \\ 93.3 & 100.4 & 98.7 & 97.4 & 98.4 & 100 & 98 & 98.4 & 97.1 & 94.4 & 99.6 \\ 5.1 & -0.2 & -0.1 & 0 & 0 & -0.3 & -0.1 & 0.2 & 0.6 & 4.8 & 0.4 \\ 1.2 & 0.4 & 1.1 & 1.3 & 1.2 & 0.4 & 1.3 & 1 & 0.1 & 0.6 & 0.3 \end{pmatrix}. \quad (a)$$

where each column is one sample and the rows are the fractional concentrations of HHb, $O_2$Hb, COHb and MetHb, respectively. The data were shifted by 0.1 nm by fitting the measured spectrum with a cubic spline and shifting the fitted spectrum. The fractional concentrations were then determined by solving equation (1) for C using the least squares method. The result was:

$$\begin{pmatrix} -0.3 & -1.3 & -0.5 & 0.4 & -0.4 & -0.8 & 0.1 & -0.4 & 1.5 & -0.5 & -1.2 \\ 93.7 & 101 & 99.3 & 98 & 99 & 100.6 & 98.6 & 98.9 & 97.6 & 94.9 & 100.2 \\ 6.1 & 0.7 & 0.8 & 1 & 0.9 & 0.6 & 0.8 & 1.1 & 1.,5 & 5.8 & 1.4 \\ 0.5 & -0.3 & 0.4 & 0.7 & 0.5 & -0.4 & 0.6 & 0.3 & -0.6 & -0.1 & -0.4 \end{pmatrix}. \quad (b)$$

The difference between the original data (a) and the shifted data (b) was determined to be:

$$\begin{pmatrix} -0.8 & -0.8 & -0.8 & -0.8 & -0.8 & -0.8 & -0.8 & -0.8 & -0.8 & -0.8 & -0.8 \\ 0.4 & 0.6 & 0.6 & 0.5 & 0.6 & 0.6 & 0.6 & 0.6 & 0.5 & 0.4 & 0.6 \\ 1 & 0.9 & 0.9 & 0.9 & 0.9 & 0.9 & 0.9 & 0.9 & 0.9 & 1 & 1 \\ 0.7 & -0.7 & -0.7 & -0.7 & -0.7 & -0.7 & -0.7 & -0.7 & -0.7 & -0.7 & -0.8 \end{pmatrix}. \quad (c)$$

As can be seen from matrix (c), the relative change in fractional concentrations due to a frequency shift as small as 0.1 nm can be quite pronounced, particularly for components that are present in relatively small concentrations.

Using the derivatives of the absorption data spectra, the shifts and concentrations were calculated on a sample by sample basis using equation (11). The results for the shift were:

$$(0.11 \; 0.04 \; 0.07 \; 0.14 \; 0.09 \; 0.15 \; 0.11 \; 0.11 \; 0.17 \; 0.09 \; 0.05), \quad (d)$$

and results for the concentrations were:

$$\begin{pmatrix} 0.6 & -1 & 0 & 1.5 & 0.3 & 0.3 & 0.9 & 0.5 & 2.8 & 0.2 & -0.7 \\ 93.2 & 100.7 & 98.7 & 97.2 & 98.5 & 99.7 & 97.9 & 98.3 & 96.7 & 94.4 & 99.9 \\ 5 & 0.3 & 0.2 & -0.3 & 0.1 & -0.8 & -0.2 & 0.2 & 0 & 4.8 & 0.9 \\ 1.2 & 0 & 0.9 & 1.6 & 1.2 & 0.7 & 1.4 & 1.1 & 0.6 & 0.5 & -0.1 \end{pmatrix}. \quad (e)$$

The difference between matrices (a) and (e) was calculated to be:

$$\begin{pmatrix} 0.1 & -0.5 & -0.2 & 0.3 & -0.1 & 0.4 & 0.1 & 0.1 & 0.5 & 0 & -0.4 \\ -0.1 & 0.3 & 0.2 & -0.2 & 0 & -0.3 & -0.1 & -0.1 & -0.4 & 0 & 0.3 \\ -0.1 & 0.6 & 0.3 & -0.3 & 0.1 & -0.4 & -0.1 & -0.1 & -0.6 & 0.1 & 0.5 \\ 0.1 & -0.4 & -0.2 & 0.3 & -0.1 & 0.4 & 0.1 & 0.1 & 0.5 & 0 & -0.4 \end{pmatrix}. \quad (f)$$

By comparing matrices (c) and (f) it is seen that the differences from the original, unshifted spectrum are much smaller when one accounts for the shift. The average shift from matrix (d) is 0.104 nm. Note that even though the individual estimates of S can vary by as much as 50%, the average value is exceptionally good.

Using the average shift of 0.104 nm to compensate for the shift in the spectrum of each sample, the fractional concentration were calculated using equation (24):

$$\begin{pmatrix} 0.5 & -0.5 & 0.3 & 1.3 & 0.4 & 0 & 0.9 & 0.4 & 2.3 & 0.3 & -0.3 \\ 93.2 & 100.4 & 98.7 & 97.4 & 98.4 & 100 & 98 & 98.3 & 97.1 & 94.4 & 99.6 \\ 5 & -0.3 & -0.1 & 0 & -0.1 & -0.4 & -0.1 & 0.2 & 0.6 & 4.7 & 0.4 \\ 1.2 & 0.4 & 1.1 & 1.4 & 1.3 & 0.4 & 1.3 & 1 & 0.1 & 0.6 & 0.3 \end{pmatrix} \quad (g)$$

and the difference between the original fractional concentrations (matrix (a)) and the fractional concentrations calculated using the average over 11 values of the shift, $\bar{S}$, (matrix (h)), was determined to be:

$$\begin{pmatrix} 0 & 0 & 0 & 0 & 0 & 0 & 0 & 0 & 0 & 0 & 0 \\ 0 & 0 & 0 & -0.1 & 0 & 0 & 0 & 0 & 0 & 0 & 0 \\ 0 & 0 & 0 & 0 & 0 & 0 & 0 & 0 & 0 & 0 & 0 \\ 0 & 0 & 0 & 0 & 0 & 0 & 0 & 0 & 0 & 0 & 0 \end{pmatrix} \quad (h)$$

Given that the avenge value of the shift was a very good estimate of the actual shift, it is not surprising that the calculated estimates of the concentrations matched the concentrations of the unshifted data so well.

Example 2

Estimating Wavelength Shift Using the Derivative of the Extinction Coefficient Matrix

Using the same data that resulted in matrix (a) in Example 1 and shifting the spectrum by 0.1 nm, we compensated for the shift by the method of calculating the derivative of the extinction coefficient matrix as described in equations (18)–(27) and associated text using estimated values of the component concentrations obtained by solving equation (19). The estimated fractional concentrations were determined to be:

$$\begin{pmatrix} 0.6 & -1.0 & 0.0 & 1.5 & 0.3 & 0.4 & 0.9 & 0.5 & 2.7 & 0.2 & -0.8 \\ 93.2 & 100.8 & 98.9 & 97.6 & 98.4 & 99.7 & 97.9 & 98.4 & 96.7 & 94.4 & 99.9 \\ 5.0 & 0.3 & 0.2 & -0.3 & 0.1 & -0.7 & -0.2 & 0.1 & 0.0 & 4.9 & 0.8 \\ 1.3 & 0.0 & 0.9 & 1.6 & 1.1 & 0.8 & 1.4 & 1.1 & 0.6 & 0.6 & 0.0 \end{pmatrix} \quad (i)$$

which differs from the original concentrations of matrix (a) as follows:

$$\begin{pmatrix} 0.1 & -0.5 & -0.2 & 0.3 & -0.1 & 0.4 & 0.1 & 0.1 & 0.5 & 0 & -0.4 \\ -0.1 & 0.4 & 0.2 & -0.2 & 0 & -0.3 & -0.1 & 0 & -0.4 & 0 & 0.3 \\ -0.1 & 0.5 & 0.3 & -0.3 & 0.1 & -0.4 & -0.1 & -0.1 & -0.6 & 0.1 & 0.4 \\ 0.1 & -0.4 & -0.2 & 0.3 & -0.1 & 0.4 & 0.1 & 0.1 & 0.5 & 0 & -0.3 \end{pmatrix} \quad (j)$$

The wavelength shifts, S, were determined to be:

$$(0.10\ 0.04\ 0.07\ 0.13\ 0.09\ 0.15\ 0.11\ 0.11\ 0.16\ 0.09\ 0.05\ 0.03). \quad (k)$$

The average shift, $\bar{S}$, is 0.097 nm.

Using the average estimated shift, $\bar{S}$, and solving for the concentrations C using equation (24) yielded the following concentrations:

$$\begin{pmatrix} 0.5 & -0.6 & 0.2 & 1.3 & 0.4 & -0.1 & 0.9 & 0.4 & 2.3 & 0.3 & -0.4 \\ 93.2 & 100.4 & 98.7 & 97.3 & 98.4 & 100 & 97.9 & 98.4 & 97 & 94.3 & 99.6 \\ 5.1 & -0.2 & -0.1 & 0 & 0 & -0.3 & -0.2 & 0.3 & 0.6 & 4.8 & 0.5 \\ 1.2 & 0.4 & 1.1 & 1.4 & 1.3 & 0.3 & 1.3 & 1 & 0.1 & 0.6 & 0.3 \end{pmatrix} \quad (l)$$

which resulted in the following differences from the original concentrations in matrix (a):

$$\begin{pmatrix} 0 & 0 & 0 & 0 & 0 & 0 & 0.1 & 0 & 0 & 0 & 0 \\ -0.1 & 0 & 0 & -0.1 & 0 & 0 & -0.1 & 0 & -0.1 & -0.1 & 0 \\ 0.1 & 0 & 0 & 0 & 0 & 0.1 & -0.1 & 0 & 0 & 0 & 0 \\ 0 & 0 & 0 & 0.1 & 0 & 0 & 0.1 & 0 & 0 & 0.1 & 0.00 \end{pmatrix} \quad (m)$$

Example 3

Averaging S Over the Previous Eight Measurements

Using the data from Example 1 and focusing on the ninth sample, one can average over the first eight samples to obtain a value of $\bar{S}$. The original fractional values for the ninth sample (obtained from the unshifted spectrum) were:

$$\begin{pmatrix} 2.2 \\ 97.1 \\ 0.6 \\ 0.1 \end{pmatrix}. \quad (o)$$

and the fractional concentrations after shifting the spectrum by 0.1 nm were:

$$\begin{pmatrix} 1.5 \\ 97.6 \\ 1.5 \\ -0.6 \end{pmatrix}. \quad (p)$$

The average shift of the first eight samples was 0.096. The fractional concentrations and wavelength shift were calculated using the derivatives of the extinction coefficients. The fractional concentrations obtained were:

$$\begin{pmatrix} 2.3 \\ 97 \\ 0.6 \\ 0.1 \end{pmatrix} \quad (q)$$

and the calculated wavelength shift was 0.06. The shift estimated for the first sample was 0.1. Continuing to average the shift over the last 8 samples, the new average shift $\bar{S}$ is given by $$\frac{0.096 \times 8 - 0.1}{7} + \frac{0.06}{8} = 0.103.$$

Using this revised figure for $\bar{S}$, the adjusted value for the extinction coefficient matrix, $E_{adj}$, was calculated and used to obtain a revised set of fractional concentrations:

$$\begin{pmatrix} 2.3 \\ 97 \\ 0.6 \\ 0.1 \end{pmatrix} \quad (r)$$

which, for this sample, differs insignificantly from the previous estimate.

We claim:

1. An improved method of determining the concentrations of one or more components of an analytical sample from an observed spectrum estimated by $$Y_{obs}(\omega) = P(\omega) \cdot C,$$

wherein $Y_{obs}$, is a vector whose "m" elements are the magnitudes of the observed spectrum at each value of an independent variable $\omega$, C is the vector whose 37 n" elements are the estimated concentrations of "n" components that contribute to the measured spectrum, and P is a "m×n" matrix whose elements are the magnitudes of the contribution to the spectrum of each of "n" components at each of the "m" values of the independent variable $\omega$, wherein the method comprises generating a sample spectrum from which the concentrations of the sample components are determined and determining the sample concentrations from the spectrum, the improvement comprising correcting for experimental error by modeling the experimental error as "r" types of errors given by the product $\xi \cdot K$ where K is a vector whose "r" elements are the magnitudes of each of the "r" types of experimental errors and $\xi$ is an "m×r" matrix whose elements are the relative errors at each value of $\omega$ for each type of experimental error, adding the product $\xi \cdot K$ to the estimated spectrum as $$Y_{obs}(\omega) = P(\omega) \cdot C + \xi \cdot K$$

and solving for the best fit values of C and K, wherein "n" and "r" are integers each greater or equal to 1 and "m" is an integer at least "n+r".

2. The method according to claim 1, wherein the best fit values of C and K are determined by least squares analysis.

3. The method according to claim 2 wherein r is 1 and the experimental error is modeled as a shift in $\omega$ by amount $d\omega$, and $\xi = Y' = (\partial Y_{obs})/(\partial \omega)$.

4. The method according to claim 2 wherein r is 1 and the experimental error is modeled as a shift in $\omega$ by an amount $d\omega, \xi = P' \cdot C$, and $$P' = \frac{\partial P}{\partial \omega}$$

5. An improved method of determining the concentrations of one or more components of an analytical sample whose observed spectrum are estimated by the equation $$Y_{obs}(\omega) = P(\omega) \cdot C$$

wherein $Y_{obs}$ is a vector whose "m" elements are the magnitudes of the observed spectrum at each value of an independent variable $\omega$, C is the vector whose "n" elements are the estimated concentrations of "n" components that contribute to the measured spectrum, and P is a "m×n" matrix whose elements are the magnitudes of the contribution to the spectrum of each of "n" components at each of the "m" values of the independent variable $\omega$, wherein the method comprises generating a sample spectrum from which the sample component concentrations are determined and determining the sample component concentrations from the spectrum, the improvement comprising correcting for experimental error by modeling the experimental error as a shift of the spectrum by an amount $d\omega$, estimating a shift, $\overline{d\omega}$, calculating an adjusted spectrum, $Y_{adj}$, using either the equation:

$$Y_{adj} = Y_{obs}(\omega + \overline{d\omega})$$

or;

$$Y_{adj} = Y_{obs} + Y' \cdot \overline{d\omega},$$

and determining the concentrations, C, by solving either the equation:

$$Y_{adj} = P \cdot C$$

or:

$$Y_{adj} = P \cdot C + \xi \cdot K$$

for the best fit value of C, where $\xi$ takes the form $\xi = Y' = (\partial Y_{obs})/(\partial \omega)$ or $\xi = P' \cdot C$, where $$P' = \frac{\partial P}{\partial \omega}$$

"m" and "n" are integers, "n" is greater or equal 1 and "m" is at least "n".

6. A method according to claim 5 wherein $\overline{d\omega}$ is the weighted average of "k" previous values of $d\omega$, wherein k is an integer greater or equal to 1, and $\overline{d\omega}$ is determined from the equation $$\overline{d\omega} = w^T \cdot d\omega^*,$$

where $w^T$ is the transpose of a vector w of length "k" whose elements are the relative weights to be applied to each of the previous "k" values of $d\omega$, $d\omega^*$ is a vector of length "k" whose elements are previously determined values of $d\omega$, and w satisfies the equation:

$$\sum_{i=1}^{k} w_i = 1.$$

7. The method according to claim 6, wherein each element of w is 1/k, or:

$$w_i = \frac{1}{a \cdot i} / \sum_{i=1}^{k} \frac{1}{a \cdot i}$$

or $$w_i = \frac{1}{a^i} / \sum_{i=1}^{k} \frac{1}{a^i}$$

where "a" is any real number greater than 1 and "i" is an integer form 1 to "k".

8. An improved method of determining the concentrations of one or more components of an analytical sample whose observed spectrum are estimated by the equation $$Y_{obs}(\omega) = P(\omega) \cdot C$$

wherein $Y_{obs}$, is a vector whose "m" elements are the magnitudes of the observed spectrum at each value of an independent variable $\omega$, C is the vector whose "n" elements are the estimated concentrations of "n" components that contribute to the measured spectrum, and P is a "m×n" matrix whose elements are the magnitudes of the contribution to the spectrum of each of "n" components ar each of the "m" values of the independent variable $\omega$, wherein the method comprises generating a sample spectrum from which the sample component concentrations are determined and determining the sample component concentrations from the spectrum, the improvement comprising correcting for experimental error by modeling the experimental error as a shift in $\omega$ by an amount $d\omega$, estimating a shift, $\overline{d\omega}$, calculating an adjusted P matrix, $P_{adj}$, using either the equation:

$$P_{adj} = P_{obs}(w + \overline{d\omega})$$

or:

$$P_{adj} = P_{obs} + P' \cdot \overline{d\omega}$$

and determining the concentrations, C, by solving either the equation:

$$Y_{obs} = P_{adj} \cdot C$$

or:

$$Y_{obs}(\omega) = P_{adj}(\omega) \cdot C + \xi \cdot K$$

for the best fit value of C, where $\xi$ takes the form $\xi = Y' = (\partial Y_{obs})/(\partial \omega)$ or $\xi = P'$ C, where $$P' = \frac{\partial P}{\partial \omega},$$

and "n" is greater or equal to 1 and "m" is at least "n".

9. A method according to claim 8 wherein the weighted average of $d\omega$, $\overline{d\omega}$, is the weighted average of k previous values of $d\omega$, wherein k is greater or equal to 1, and determined from the equation $$\partial \omega = w^T \cdot d\omega^*,$$

wherein $w^T$ is the transpose of a vector w of length "k" whose elements are the relative to be applied to each of the previous k values of $d\omega$, wherein "k" is an integer greater or equal to 1, $d\omega^*$ is a vector of length "k" whose elements are the previously determined values of $d\omega$, and w satisfies the equation:

$$\sum_{i=1}^{k} w_i = 1.$$

10. The method according to claim 9, wherein each element of w is 1/k, or:

$$w_i = \frac{1}{a \cdot i} / \sum_{i=1}^{k} \frac{1}{a \cdot i}$$

or $$w_i = \frac{1}{a^i} / \sum_{i=1}^{k} \frac{1}{a^i}$$

wherein "a" is any real number greater than 1, and "i" is an integer from 1 to "k."

11. The method according to any claims 3, 4, 6, or 9, wherein the shift in $\omega$ is modeled as constant across the entire spectrum and equal to a scalar $d\omega = S$.

12. The method according to claim 11, wherein Y is an absorbance spectrum of the sample, P is the extinction coefficient matrix for the absorbing components of the sample, and $\omega$ is the frequency at which the absorbance is measured.

13. The method according to any of claims 3, 4, 6, or 9, wherein the shift in $\omega$ is modeled as $d\omega_i = (\omega_i - \omega_c)M$, wherein $d\omega_i$ is the shift at the $i^{th}$ value of $\omega$, $\omega_i$ is the $i^{th}$ value of $\omega$, $\omega^c$ is a constant value of $\omega$, and M, which is any real number, is the magnitude of the error.

14. The method according to claim 13, wherein Y is an absorbance spectrum of the sample, P is the extinction coefficient matrix for the absorbing components of the sample, and $\omega$ is the frequency at which the absorbance is measured.

15. An apparatus for determining the concentration of components in a sample comprising
   a means for generating a spectrum from the sample;
   a means for detecting the spectrum;
   a means for recording the spectrum; and
   a means for determining the concentrations of sample components from the spectrum according to the method of claim 12.

16. The apparatus according to claim 15, wherein the apparatus comprises a spectrophotometer generating a sample spectrum in the UV, VIS, or IR regions of the electromagnetic spectrum.

17. An apparatus for determining the concentration of components in a sample comprising
   a means for generating a spectrum from the sample;
   a means for detecting the spectrum;
   a means for recording the spectrum; and
   a means for determining the concentrations of sample components from the
   spectrum according to the method of claims 14.

18. The apparatus according to the claims 17, wherein the apparatus comprises a spectrophotometer generating a sample spectrum in the UV, VIS, or IR regions of the electromagnetic spectrum.

* * * * *